US008772248B2

(12) United States Patent
Bailey

(10) Patent No.: US 8,772,248 B2
(45) Date of Patent: Jul. 8, 2014

(54) DRUG DELIVERY SYSTEM

(75) Inventor: Patrick Dawson Bailey, Macclesfield (GB)

(73) Assignee: Keele University, Staffordshire (GB)

( * ) Notice: Subject to any disclaimer, the term of this patent is extended or adjusted under 35 U.S.C. 154(b) by 1415 days.

(21) Appl. No.: 10/585,864

(22) PCT Filed: Jan. 17, 2005

(86) PCT No.: PCT/GB2005/000151
§ 371 (c)(1),
(2), (4) Date: Jul. 11, 2006

(87) PCT Pub. No.: WO2005/067978
PCT Pub. Date: Jul. 28, 2005

(65) Prior Publication Data
US 2008/0139670 A1   Jun. 12, 2008

(30) Foreign Application Priority Data

Jan. 17, 2004   (GB) .................................. 0401008.8

(51) Int. Cl.
*A61K 38/05* (2006.01)
(52) U.S. Cl.
USPC ........................................................ 514/21.91
(58) Field of Classification Search
None
See application file for complete search history.

(56) References Cited

U.S. PATENT DOCUMENTS

| 5,457,180 | A |   | 10/1995 | Zacharie |   |
|---|---|---|---|---|---|
| 5,606,017 | A | * | 2/1997 | Willner et al. | 530/322 |
| 5,662,911 | A | * | 9/1997 | Huber et al. | 424/278.1 |
| 2003/0220245 | A1 | * | 11/2003 | Hubbell et al. | 514/12 |

FOREIGN PATENT DOCUMENTS

| WO | WO 91/01976 | 2/1991 |
|---|---|---|
| WO | WO 99/20649 | 4/1999 |

OTHER PUBLICATIONS

Mcelroy et al ('Gly-(CSNH)-Phe resists hydrolysis by membrane dipeptidase' Biochemical Society Transactions (1998) 26(1) S31).*
Benzene fact sheet (retrieved from http://www.epa.gov/safewater/pdfs/factsheets/voc/tech/benzene.pdf on Aug. 19, 2013, 4 pages).*
International Search Report dated Jun. 22, 2006, issued in connection with PCT/GB2005/000151.
Meredith et al, "4-Aminomethylbenzoic acid is a non-translocated competitive inhibitor of the epithelial peptide transporter PepT1", *Journal of Physiology*, 1998, 512, 3, pp. 629-634.
Pieri et al, "Site-directed mutagenesis of Arginine282 suggests how protons and peptides are co-transported by rabbit PepT1", *International Journal of Biochemistry & Cell Biology*, 2008, 40, pp. 721-730.
Hidalgo et al, "Characterization of the Human Colon Carcinoma Cell Line (Caco-2) as a Model System for Intestinal Epithelial Permeability", *Gastroenterology*, 1989, 96, pp. 736-749.
Lister et al, "Dipeptide transport and hydrolysis in isolated loops of rat small intestine: effects of stereospecificity", *Journal of Physiology*, 1995, 484.1, pp. 173-182.
Li et al, "Molecular modeling study of structural requirements for the oligopeptide transporter", *Journal of Drug Targeting*, 1996, 4, 1, pp. 9-17.
Swaan et al, "Molecular Determinants of Recognition for the Intestinal Peptide Carrier", Journal of Pharmaceutical Sciences, 1997, 86, No. 5, pp. 596-602.
Daniel, "Molecular and Integrative Physiology of Intestinal Peptide Transport", *Annu. Rev. Physiol.*, 2004, 66, pp. 361-384.
Brandsch et al, "Pharmaceutical and pharmacological importance of peptide transporters", *Journal of Pharmacy and Pharmacology*, 2008, 60, pp. 543-585.
Bailey et al, "How to Make Drugs Orally Active: a Substrate Template for Peptide Transporter PepT1", *Angewandte Chemie, Int. Ed. Engl.*, 2000, 39, No. 3, pp. 506-508.
Bailey et al, "Affinity prediction for substrates of the peptide transporter PepT1", *Chemical Communications*, 2006, pp. 323-325.
Thomsen et al, "Acyclovir prodrug for the intestinal di/tri-peptide transporter PEPT1: comparison of in vivo bioavailability in rats and transport in Caco-2 cells", *European Journal of Pharmaceutical Science*, 2004, 23, pp. 319-325.
Nakamura et al, "Stereochemistry and Total Synthesis of Dolastatin E", Tetrahedron Letters, vol. 36, No. 28, 1995, pp. 5059-5062.
McKeever et al, "Total synthesis of the prenylated cyclopeptide trunkamide A, a cytotoxic metabolite from *Lissoclinum* sp.", Tetrahedron Letters 42 (2001) 2573-2577.
Le et al, "Design of potent dynorphin A-(1-9) analogues devoid of supraspinal motor effects in mice", Canadian Journal of Physiology and Pharmacology, vol. 75, No. 1, 1997, pp. 9-14.
Clausen et al, "Studies on Amino Acids and Peptides. Part 6.[1] Methods for Introducing Thioamide Bonds into the Peptide Backbone: Synthesis of the Four Monothio Analogues of Leucine Enkephalin", Journal of the Chemical Society Perkin Transactions I, No. 4, 1984, pp. 785-798.
Lehmann et al, "Synthesis of Endothiopeptides and Their Cyclization to 1,3-Thiazol-5(4H)-imines", Helvetica Chimica Acta 1999 Switzerland, vol. 82, No. 11, 1999, pp. 1899-1915.
Zacharie et al, "Thioamides: Synthesis, Stability, and Immunological Activities of Thioanalogues of Imreg. Preparation of New Thioacylating Agents Using Fluorobenzimidazolone Derivatives", Journal of Medicinal Chemistry, vol. 42, No. 11, 1999, pp. 2046-2052.
Lajoie et al, "Facile Regioselective Formation of Thiopeptide Linkages from Oligopeptides with New Thionation Reagents", Tetrahedron Letters, vol. 24, No. 36, 1983, pp. 3815-3818.

(Continued)

*Primary Examiner* — James H Alstrum Acevedo
*Assistant Examiner* — Ronald Niebauer
(74) *Attorney, Agent, or Firm* — Swanson & Bratschun, L.L.C.

(57) ABSTRACT

A compound comprises a thiopeptide, or derivative or analogue thereof, the thiopeptide comprising a C-terminal carboxylic acid group, and a functional group for attachment to a drug, characterized in that the compound is adapted to carry or transport a drug.

11 Claims, 7 Drawing Sheets

(56) References Cited

OTHER PUBLICATIONS

Brown et al, "Mono- and Dithionopeptide Synthesis", Tetrahedron Letters, vol. 28, No. 19, 1987, pp. 2171-2174.

Zacharie et al, "Thioacylating Agents. Use of Thiobenzimidazolone Derivatives for the Preparation of Thiotuftsin Analogs", Tetrahedron, Vo. 49, No. 46, 1993, pp. 10489-10500.

La Cour, "Stereochemistry of peptides containing a thioacyl group", International Journal of Peptide and Protein Research, vol. 30, No. 4, 1987, pp. 564-571.

Elmore et al, "Thioesters of Amino Acid Derivatives as Thioacylating Agents in Thiopeptide Synthesis", Journal of the Chemical Society, Perkin Transactions 1, No. 5, 1988 pp. 1051-1055.

Campbell et al, "Carboxypeptidase a Catalyzed Hydrolysis of Thiopeptide and Thionester Analogues of Specific Substrates. An Effect on $k_{cat}$ for Peptide, but Not Ester, Substrates", Journal of the American Chemical Society, vol. 104, No. 19, 1982, pp. 5221-5226.

Lehmann et al, "Site-Selective Incorporation of Thioamide-Linkages into a Growing Peptide", Tetrahedron, vol. 55, No. 17, 1999, pp. 5359-5376.

Yao et al, "Endothiopeptide Inhibitors of HIV-1 Protease", Bioorganic & Medicinal Chemistry Letters, vol. 8, No. 6, 1998, pp. 699-704.

McKeever et al, "Total synthesis of trunkamide A, a novel thiazoline-based prenylated cyclopeptide metabolite from *Lissoclinum* sp." Tetrahedron, vol. 59, No. 15, 2003, pp. 2713-2727.

* cited by examiner

Selected synthetic thiopeptide targets prepared as drug carrier models

Figure 7

| Entry | Type | Binding $K_i$/mM | Transport (cf Gly-Gln)† |
|---|---|---|---|
| 1 | A | 1.41 | |
| 2 | A | 0.29 | |
| 3 | A | 0.37 | |
| 4 | A | 0.09 | |
| 5 | A | 0.34 | < |
| 6 | A | 0.53 | |
| 7 | A | 1.05 | |
| 8 | B | 0.3 | = |
| 9 | B | 0.2 | = |
| 10 | B | 0.12 | = |
| 11 | B | 0.11 | = |
| 12 | B | 0.03 | < |
| 14 | B | 0.1 | < |
| 15 | B | 0.09 | = |
| 16 | B | 0.6 | < |
| 17 | B | 0.23 | < |
| 18 | B | 0.2 | = |
| 19 | B | 0.13 | < |
| 20 | B | 0.16 | = |
| 22 | B | 0.09 | > |
| 23 | B | 0.11 | = |
| 24 | B | 0.08 | |
| 25 | B | 0.12 | = |
| 26 | B | 0.36 | < |
| 28 | B | 0.05 | = |
| 29 | B | n.d.* | < |
| 30 | B | n.d.* | = |
| 31 | C | 0.61 | |
| 32 | C | 0.25 | |
| 33 | C | 0.09 | |
| 34 | C | 1.58 | |
| 35 | C | 0.19 | = |
| 36 | C | 2.32 | < |
| 37 | C | 0.93 | |
| 41 | E | 0.03 | |
| 42 | F | 0.09 | < |
| 43 | F | 0.15 | = |
| 45 | G | 0.24 | > |
| 46 | G | 0.07 | > |
| 47 | G | 0.22 | = |
| 48 | H | 1.3 | = |
| 49 | H | 4.69 | = |
| 50 | I | 0.15 | > |
| 51 | I | 2.5 | |
| 52 | I | 9.7 | = |

\* 29B/30B are strong inhibitors (est. $K_i$ < 1mM), but are too insoluble for accurate $K_i$ determination.

† Efflux of radio-labelled D-Phe-L-Gln is a positive indication of active transport via PepT1 (although negative results do not necessarily mean that substrates are not transported). In these assays (see elsewhere for details), the dipeptide Gly-Gln (which is known to be transported) caused ca 30% of labelled D-Phe-L-Gln to remain in the oocytes; at the same concentration, substrates were assessed as:
    < (measurable efflux, but less transport than Gly-Gln, with ≥50% of D-Phe-L-Gln remaining)
    = (efflux similar to the effect of Gly-Gln – i.e. 25-50% of labelled D-Phe-L-Gln remaining)
    > (more efflux than Gly-Gln – i.e. <25% of labelled D-Phe-L-Gln remaining)

DRUG DELIVERY SYSTEM

This application is the US national phase of international application PCT/GB2005/000151, filed 17 Jan. 2005, which designated the U.S. and claims priority of GB 0401008.8, filed 17 Jan. 2004, the entire contents of each of which are hereby incorporated by reference.

The present invention relates to drug delivery systems and particularly, although not exclusively, to drug delivery systems which exploit the PepT1 pathway. More specifically, the invention relates to novel peptides and peptide analogues/derivatives, for use as peptide drug carrier molecules, and peptide drug carrier-drug conjugates which are transported across the wall of the gut into the blood by PepT1 protein, and uses thereof in medicine. The invention further extends to methods of synthesising such peptide drug carriers.

A large proportion of drugs used in medicine, that are orally administered, are subject to structural modification and, in some cases, substantial degradation in the gut, and this can often lead to a decrease in the biological activity of the drug. Accordingly, the medicinal efficacy of such drugs can be limited when taken orally. Furthermore, a large number of drugs that exhibit medicinal properties cannot be administered to a patient orally because they have poor solubility, or they are unable to diffuse across the wall of the gut into the bloodstream. Therefore, unfortunately, such drugs are either totally rejected for use in medical treatment, or have to be administered to patients by intravenous injection, which is invasive and has associated problems with many patients. Accordingly, there is a need to develop mechanisms by which drugs, which are either injected intravenously, or are not used at all, can be administered orally and transferred into the blood via the gut without any loss in biological activity. In addition, there is a need to improve the transportation of drug molecules across the wall of the gut in respect of those drugs which are currently administered orally, but which show decreased or low levels of medicinal activity.

PepT1 is a trans-membrane protein that is highly expressed in the jejunum region of the small intestine, and transports small peptides, such as the breakdown products of protein in food, across the wall of the gut into the bloodstream. PepT1 transports di-peptides and tri-peptides across the gut wall efficiently. Substrate transportation by PepT1 is driven by proton and electrochemical gradients and provides a mechanism by which peptidic drugs such as β-lactam antibiotics, and ACE inhibitors, for example, Captopril, can be orally absorbed by patients. Accordingly, drugs that do not naturally diffuse across the villi of the small intestine, or those which have poor solubility, and which are only administerable by intravenous injection may be made orally administrable by transporting them across the wall of the gut into the bloodstream via the PepT1 pathway. In addition, the PepT1 pathway may also be exploited to improve the transportation of drugs which are currently administered orally, but which show decreased levels of biological activity, for example, because they are modified or degraded in the gut before they are transported into the blood.

Therefore, it is an aim of embodiments of the present invention to address the above problems and problems with the prior art, and to provide a drug delivery system, which could be made available to the medical community, so that drugs, which are normally administered orally but which exhibit reduced or low levels of medicinal activity can have their performance improved. In addition, the drug delivery system could also enable drugs that are administered intravenously or which are not used at all, to be administered orally.

According to a first aspect of the present invention, there is provided a compound comprising a thiopeptide, or derivative or analogue thereof, the thiopeptide comprising a C-terminal carboxylic acid group, and a functional group for attachment to a drug, characterised in that the compound is adapted to carry or transport a drug.

Preferably, the compound is adapted to, or is capable of carrying or transporting a drug, preferably in vivo. The term "drug" as used herein is intended to encompass any pharmaceutically or medicinally active compound or molecule. For example, the drug may have a poor solubility, or may be too polar to cross a membrane when in use. Examples of suitable drugs, which may be used in accordance with the invention may include antivirals, antibiotics, β-blockers, neurotransmitters, hormonal, and anti-cancer drugs. Preferred examples of drugs may include adrenaline, dopamine, GABA, acyclovir, sulfonamides, enalaprilate, burimamide-based $H_2$ antagonists, propranolol, bestatin, or steroidal drugs.

Advantageously, and preferably, the thiopeptide compound according to the first aspect enables drugs, which are either not used at all in medicine, or which have to be administered intravenously, to be administered to a patient orally. In addition, advantageously, the thiopeptide compound improves the performance of drugs, which may be normally administered orally, but which may exhibit reduced or low levels of medicinal activity when taken orally, such as drugs with poor solubility. Administering drugs orally, i.e. by mouth, is much simpler and less invasive than by intravenous injection, which is very off-putting for the majority of patients, and has a range of other health risks. Therefore, advantageously, use of the compound according to the present invention, will greatly increase the number of drugs that can be used, and administered orally.

The inventors have found that the compound according to the present invention may have a drug molecule attached to the functional group of the thiopeptide, thereby forming a 'compound-drug' conjugate. In addition, the inventors have found that this conjugate-drug has improved transportation properties, for example, across the wall of the gut. The inventors do not wish to be bound by any hypothesis, but believe that the conjugate may be transportable, moved or carried from a first site to a second site by an active transport mechanism. An example of an active transport mechanism is a symporter, which may be a proton-dependant symporter. In particular, the inventors believe that such conjugates may be transported via the PepT1 pathway. Accordingly, the compound is preferably adapted to act as a PepT1 substrate.

PepT1 is most strongly expressed in the jejunum of the small intestine. However, PepT1 has also been isolated from the liver, brain, and from the cortex and medulla of the kidneys. Hence, it will be appreciated that the compound in accordance with the invention may be transported in any of the gut, liver, brain, or in the kidneys etc, and as such, the compound may be transported in any of these tissues. However, in a preferred embodiment, the compound according to the invention may be transported across the lining of the gut, for example, in the small intestine, and particularly, in the jejunum.

A second isoform, Pep2, which shares approximately 50% sequence homology with PepT1, has also been found in the kidneys, where it reabsorbs peptides from the glomerular filtrate. Therefore, it will be appreciated that the compound according to the invention will also have the advantageous properties of being able to exploit the PepT2 pathway, being transported thereby.

Brandsch et al. (J. Biol. Chem., Vol. 273, 3861-3864, 1998), discloses a thio-Phe-Pro thiopeptide and uses thereof in the investigation of the conformational requirements for substrates for PepT1. Brandsch et al. supra do not demonstrate attachment of a drug molecule to the thiopeptide, hydrolysis resistance of the thiopeptide, nor any drug carrying or any drug transportation by the thiopeptide. Accordingly, the compound in accordance with the present invention shows significant surprising advantages over the thiopeptide disclosed in Brandsch et al. supra due to the ability of the compound according to the first aspect to be attached to a drug via its functional group, and the compound's ability to transport a drug in vivo.

Preferably, the thiopeptide comprises at least two amino acids or derivatives or analogues thereof, or at least three amino acids or derivatives or analogues thereof, or at least four amino acids or derivatives or analogues thereof. Hence, the compound may comprise a dipeptide or a tripeptide or derivatives or analogues thereof. Accordingly, the compound may comprise a thiodipeptide or a thiotripeptide or derivatives or analogues thereof. Preferably, the compound comprises a dipeptide. Hence, it is most preferred that the compound comprises a thiodipeptide. Advantageously, thiodipeptides are conveniently small molecules compared to longer peptides, and are therefore relatively simple to synthesise. Moreover, due to their small size, they also exhibit good transportation properties via the PepT1/PepT2 pathway.

The amino acids may be selected from the repertoire of twenty amino acids commonly found in proteins. The compound may comprise an acidic or a basic amino acid. The compound may comprise a hydrophobic or a hydrophilic amino acid. Preferably, the compound comprises a serine, aspartate or glutamate residue as the second or C-terminal residue.

The inventors have found that a serine, aspartate, or glutamate residue represents an advantageous means of attaching a drug to the thiopeptide.

Preferably, the thiopeptide comprises at least one thio group, which thio group is preferably attached at, or towards, an N-terminal thereof. However, the thio group may be attached at, or towards, the C-terminal of the thiopeptide. Preferably, the thio group substitutes a carbonyl group on the thiopeptide. Preferably, the oxygen of a peptide bond between adjacent residues of the peptide is replaced by sulphur, to generate the thiopeptide. The thiopeptide may comprise more than one thio group, for example, two or more thio groups. Hence, where the thiopeptide comprises two amino acids, the oxygen of a peptide bond between the two residues of the peptide is replaced by sulphur, to generate the thiopeptide. Where the thiopeptide comprises three amino acids, the oxygen of a peptide bond between first and second and/or second and third residues of the peptide may be replaced by sulphur, to generate the thiopeptide, and so on. It is preferred that the peptide bond between the first and second amino acid residues is replaced by sulphur.

Advantageously, the effects of the sulphur atom of the at least one thio group in the thiopeptide are that:—
  (i) it allows surprisingly efficient binding of a compound-drug conjugate to a transporter;
  (ii) it renders the conjugate substantially resistant to hydrolysis, unlike most peptides; and
  (iii) it allows surprisingly rapid in vivo transport of the conjugate across the wall of the gut into the bloodstream.

It is most preferred that the compound comprises a thiodipeptide, which comprises two amino acid residues linked together. However, the thiodipeptide is not technically speaking a peptide because it may be considered to lack a peptide bond (CONH) where the two amino acid residues are linked to each other. This is because of the presence of the thio group, which substitutes the carbonyl group (CO) on one of the two residues of the resultant thiopeptide forming a CSNH bond. By the term "thiopeptide" used herein, we mean at least two amino acids joined together, comprising at least one thio-functional group. When the compound comprises a dipeptide, the thiopeptide may be considered to comprise no peptide bonds, (i.e. only a CSNH bond).

Where the thiopeptide comprises a plurality of amino acid residues bonded together, preferably, the number of peptide bonds in the peptide is kept to a minimum. Preferably, the thiopeptide comprises less than four peptide bonds, more preferably, less than three peptide bonds, even more preferably, less than two peptide bonds, and most preferably, no peptide bonds. For example, a CSNH bond is formed where a peptide bond would have been formed by the condensation of two amino acids. For example, when the compound comprises a tripeptide, the thiopeptide may be considered to have one or no peptide bonds, and one or two thio (CSNH) bonds.

Advantageously, and preferably, the compound is substantially resistant to hydrolysis, for example, by peptidases, because the thiopeptide compound has either few peptide bonds or no peptide bonds at all, which would otherwise be digested by peptidases. It is preferred that the compound comprises a thiodipeptide, or derivative or analogue thereof, characterised in that a thiopeptide bond substitutes a peptide (CONH) bond, wherein the C-terminal residue of the peptide comprises serine.

It is preferred that the compound comprises a thiodipeptide, or derivative or analogue thereof, characterised in that a thio (CSNH) bond substitutes a peptide (CONH) bond, wherein the C-terminal residue of the peptide comprises an acidic amino acid, for example, aspartate or glutamate.

The compound may have formula I:—

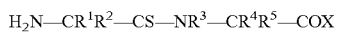
$$H_2N-CR^1R^2-CS-NR^3-CR^4R^5-COX$$

wherein $R^1$, $R^2$, $R^3$, $R^4$, and $R^5$ may be independently selected from a group consisting of a hydrogen; a linear or branched alkyl group; a dialkyl group; a N-alkyl group; and a side chain group of an amino acid residue; and wherein X may be independently selected from a hydroxyl group; an amino acid residue; an amide; an amide link to a third residue; a peptide; and a thiopeptide.

It is preferred that $R^2$ may be hydrogen. It is preferred that $R^3$ may be hydrogen. It is preferred that $R^5$ may be hydrogen. It is preferred that X may be a hydroxyl group.

Hence, in a preferred embodiment, the compound may have formula II:—

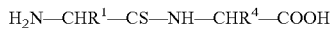
$$H_2N-CHR^1-CS-NH-CHR^4-COOH$$

wherein $R^1$, and $R^4$ may be independently selected from a group consisting of a hydrogen; a linear or branched alkyl group; a dialkyl group; a N-alkyl group; an alkoxy group; and a side chain group of an amino acid residue.

Preferably, in a most preferred embodiment, the compound may have formula II:—

$$H_2N-CHR^1-CS-NH-CHR^4-COOH$$

wherein $R^1$, and $R^4$ may be independently selected from a group consisting of a hydrogen; a linear or branched alkyl group; an alkyl chain attached to other functional groups; and a side chain group of an amino acid residue. Examples of suitable functional group include amine; amide; ester; acid; alcohol; ether; thiol; thioether; and aryl, or aromatic compounds.

It will be appreciated that $R^1$ and $R^4$ are functional groups on first and second amino acid residues of the thiopeptide, respectively.

Preferably, $R^4$ is adapted to be attached to a drug molecule. In a preferred embodiment, $R^4$ comprises or contains an alcohol or a carboxylic acid group. Preferably, $R^4$ comprises an alkyl chain, which alkyl chain is attached to an alcohol or a carboxylic acid group. The alkyl group or alkyl chain may comprise a $C_1$-$C_{20}$ chain, and preferably, a $C_1$-$C_{15}$ chain. It is envisaged that the alkyl group or the alkyl chain may comprise a $C_1$-$C_{10}$ chain, and more preferably, a $C_1$-$C_6$ chain, and most preferably a $C_1$-$C_3$ chain. The chain may be straight or branched. However, preferably, the chain is straight. The alkyl group or alkyl chain may be a methyl, ethyl, propyl, butyl, or a pentyl chain.

Preferably, $R^4$ comprises a side chain group of an amino acid residue. It is especially preferred that $R^4$ comprises an amino acid side chain group of a DNA encoded amino acid. The amino acid side chain group of $R^4$ may be independently selected from an amino acid side chain group of an acidic, basic, hydrophobic or a hydrophilic amino acid residue.

It is preferred that $R^4$ is an amino acid side chain comprising an alcohol or a carboxylic acid group. Hence, in a preferred embodiment, $R^4$ is an amino acid side chain, which incorporates either an alcohol or a carboxylic group. Accordingly, it is preferred that $R^4$ comprises an amino acid side chain group independently selected from a group consisting of serine; threonine; glutamic acid; aspartic acid; and tyrosine. Most preferably, $R^4$ comprises an amino acid side chain group of serine; glutamic acid; or aspartic acid.

$R^4$ may comprise spacing means, which spacing means is adapted to distance the drug away from the thiopeptide when bound thereto, and preferably the C-terminal amino acid thereof. This may be advantageous, for example, in cases where it is not easy to attach a particular drug to the reactive group of $R^4$, and this may depend on the particular structure and/or type of drug being attached thereto. In such a case, it would be useful to either (i) attach the drug molecule to a spacing means, and then attach the spacing means together with the drug to $R^4$; or (ii) have a spacing means on $R^4$, with the reactive group of $R^4$ towards, or on, the end of the spacing means. The thiopeptide-drug conjugates illustrated in FIG. 6 (specifically, groups F, G, H and I) each comprise suitable spacing means in accordance with the invention.

The skilled technician will appreciate the types of chains, which may be incorporated in the compound as a spacing means or spacer. For example, the spacing means may comprise an alkyl chain, or an alkyl chain incorporating ether, amino, ester, amide or carbonyl groups, with appropriate functionalisation at it's termini for attachment to the thiopeptide compound, and also preferably, the drug molecule. The attachment of the spacing means to the thiopeptide and drug may be, for example, by an ester linkage.

The spacing means may comprise at least one, preferably at least two, and more preferably, at least three atoms in a chain. It will be appreciated that the actual type of atom is less important than the number and size of the atom, which impart the distancing effect of the drug away from the thiopeptide. Hence, by way of example, the atom(s) in the spacing means may be a carbon or oxygen atom, or combinations thereof.

The spacing means may comprise a straight or branched chain. However, preferably, the chain is straight. It is envisaged that the spacing means or spacer may comprise at least 5, 10, 15, 20, 25, or 30 or more atoms. It will be appreciated that the formula and length of the spacer will be determined by the type of drug molecule to be attached to the thiopeptide.

The spacing means may comprise a repeated unit, or chain. For example, the spacing means may comprise $[—CH_2—]_n$, wherein the value of n is an integer of at least 1. However, n is an integer, which may be greater than 1, and hence, is essentially a repeated unit of $[—CH_2—]_n$. Another example of a suitable spacing means comprises $[—CH_2—O—CH_2—]_n$, wherein n is an integer of at least one. However, n is an integer, which may be greater than 1, and hence, is essentially a repeated unit of $CH_2—O—CH_2—]_n$.

Advantageously, and preferably, when a drug molecule is attached to the $R^4$ group of the thiopeptide, the thiopeptide comprises a C-terminal COOH group, which is preferred for substrate recognition by PepT1 protein, and transportation thereby. The Example and FIG. 2 shows a structure of a substrate for PepT1, which preferably comprises a thiodipeptide with a C-terminal carboxylic acid group.

Preferably, $R^1$ comprises an alkyl chain. The alkyl group or alkyl chain may comprise a $C_1$-$C_{20}$ chain as defined herein. $R^1$ may comprise a side chain group of any amino acid residue. It is especially preferred that $R^1$ comprises an amino acid side chain group of a DNA encoded amino acid. $R^1$ may comprise a side chain group independently selected from an amino acid side chain group of an acidic, basic, hydrophobic or a hydrophilic amino acid residue. For example, the amino acid side chain group may be independently selected from a group consisting of (i) H (glycine); (ii) Me (alanine); (iii) $CH_2Ph$ (phenylalanine); (iv) $CHMe_2$ (valine); (v) $CH_2OH$ (serine); (vi) $CH_2SH$ (cysteine); (vii) $CH_2CO_2H$ (aspartate); (viii) $CH_2CONH_2$ (asparagine); and (ix) $(CH_2)_4NH_2$ (lysine).

In a preferred embodiment, $R^1$ is selected from any of the side chain groups shown in column D in FIG. 1.

In a preferred embodiment, $R^1$ and $R^4$ may be a side chain group of any amino acid residue. It is envisaged that $R^1$ and $R^4$ may be the same as each other, or different from each other.

FIG. 6 illustrates a selection of preferred thiopeptides in accordance with the invention. For example, in a preferred embodiment, the thiopeptide may comprise a thiodipeptide comprising alanine as the first amino acid residue, and serine as the second amino acid residue. The drug is attached to the reactive group of the serine residue.

In another preferred embodiment, the thiopeptide may comprise alanine as the first amino acid residue, and aspartate as the second amino acid residue. The drug molecule is attached to the reactive group of the aspartate residue.

In another preferred embodiment, the thiopeptide may comprise alanine as the first amino acid residue, and glutamate as the second amino acid residue. The drug molecule is attached to the reactive group of the glutamate residue.

The functional group to which a drug is to be attached may be protected by a protection group, preferably prior to attachment of the drug thereto. Suitable protection groups may include t-butyl, benzyl, methoxybenzyl, allyl or fluorenyl attached to nitrogen, oxygen or sulphur via ester, thioether, or carbamate linkages. The functional group may be deprotected before attachment of a drug to the compound by the addition of a suitable reducing agent. The reducing agent may comprise a one electron reducing agent. For example, when benzyl-type protection is to be removed, the use of a suitable reducing agent comprising sodium/liquid ammonia is found to be effective, without significant reaction with the thiopeptide functional group. De-protection results in the freeing up of the functional group ready for attachment of the drug.

Derivatives or analogues of the thiopeptide compound according to the invention may include derivatives or analogues that increase or decrease the peptide's half-life in vivo. It is preferred that the derivative or analogue exhibits enhanced resistance to hydrolysis, by for example, peptidases. Examples of derivatives or analogues capable of increasing the half-life of the peptide according to the invention include peptoid derivatives, D-amino acid derivatives of the peptides, and peptide-peptoid hybrids.

The thiopeptide according to the invention may be subject to degradation by a number of means (such as protease activity in biological systems). Such degradation may limit the bioavailability of the peptide, and hence the ability of the peptide to achieve its biological function. There are wide ranges of well-established techniques by which peptide derivatives or analogues that have enhanced stability in biological contexts can be designed and produced. Such peptide derivatives may have improved bioavailability as a result of increased resistance to protease-mediated degradation. Preferably, a peptide derivative or analogue suitable for use according to the invention is more protease-resistant than the peptide from which it is derived. Protease-resistance of a peptide derivative and the peptide from which it is derived may be evaluated by means of well-known protein degradation assays. The relative values of protease resistance for the peptide and the peptide derivative or analogue may then be compared.

Peptoid derivatives of the thiopeptide of the invention may be readily designed from knowledge of the structure of the peptide. Peptoid compounds have two properties that make them suitable for use as peptide derivatives/analogues according to the invention:—
 (i) In peptoid residues, no hydrogen bond involving the NH would be possible.
 (ii) The peptoids are resistance to enzymatic degradation.

Commercially available software may be used to develop peptoid derivatives according to well-established protocols.

Retropeptoids, (in which all amino acids are replaced by peptoid residues in reversed order) are also able to mimic peptides. A retropeptoid is expected to bind in the opposite direction in the ligand-binding groove, as compared to a peptide or peptoid-peptide hybrid containing one peptoid residue. As a result, the side chains of the peptoid residues are able to point in the same direction as the side chains in the original peptide.

A further embodiment of a modified form of peptide according to the invention comprises D-amino acid forms of the peptide. For example, at least one of the amino acid residues in the thiopeptide is a D-isomer. It is preferred that the first amino acid residue is a D-isomer, for example, D-alanine, as described in the Examples. If the thiopeptide is a tripeptide, at least two of the amino acid residues may be D-isomers. Hence, the derivative, or analogue of the corresponding thiopeptide preferably exhibits enhanced resistance to hydrolysis. The preparation of peptides using D-amino acids rather than L-amino acids greatly decreases any unwanted breakdown of such an agent by normal metabolic processes, decreasing the amounts of agent which need to be administered, along with the frequency of its administration.

According to a second aspect of the present invention, there is provided a drug carrier comprising a thiopeptide, or derivative or analogue thereof.

Preferably, the thiopeptide, or derivative or analogue thereof comprises the thiopeptide, or derivative or analogue thereof according to the first aspect. Preferably, the thiopeptide, or derivative or analogue thereof, comprises a C-terminal carboxylic acid group, and preferably, a functional group for attachment to a drug. Preferably, the compound is adapted to carry or transport a drug. It is preferred that the drug carrier comprises a thiodipeptide or a thiotripeptide. Preferably, a C-terminal amino acid residue of the thiopeptide is adapted to be attached to a drug molecule. Preferably, the functional group is present at, or towards, the C-terminal of the thiopeptide.

The amino acids may be selected from the repertoire of twenty amino acids commonly found in proteins, or other non-DNA encoded amino acids. The compound may comprise an acidic or a basic amino acid. The compound may comprise a hydrophobic or a hydrophilic amino acid. Preferably, the compound comprises a serine, glutamate or an aspartate residue, preferably as the second residue, for example, when the thiopeptide is a dipeptide. Preferably, the thiopeptide comprises at least one thio group, which may be present on the N-terminal residue, preferably substituting a carbonyl group of the peptide.

Preferably, the functional group comprises an alcohol or a carboxylic group which is adapted to be attached to a drug molecule.

The drug carrier may have a formula I, and preferably formula II according to the first aspect.

According to a third aspect of the invention, there is provided a drug conjugate comprising a drug, which drug is linked to a compound according to the first aspect or a drug carrier according to the second aspect.

Hence, the compound according to the first aspect or the drug carrier according to the second aspect may be adapted to be attached to a drug molecule, thereby forming a 'compound-drug' or a 'drug carrier-drug' conjugate, hereinafter referred to as a 'drug conjugate'. Preferably, the attachment of the drug to the compound or drug carrier is by covalent bonding. It will be appreciated by the skilled technician that covalent bonding between the drug molecule and the compound according to the first aspect or the drug carrier according to the second aspect may be achieved by reacting a functional or reactive group on the compound or drug carrier, and a functional or reactive group on the drug. Preferably, the compound or drug carrier comprises at least one functional group, which functional group is adapted to react with the drug molecule. The functional group on the compound or drug carrier may be present on the N-terminal or C-terminal residue of the thiopeptide. The skilled technician will appreciate the types of functional or reactive groups, which would react with the drug molecule. For example, the at least one functional group may be an oxygen group, a carbonyl group, a hydroxyl group or a carboxylic acid group, which may be present on either the first or second amino acid residue.

It should be appreciated that the present invention does not extend to the selection of the drug itself. The inventors did not investigate the biological activity of any drug molecule being attached to the compound according to the first aspect or the carrier according to the second aspect. The inventors tested a number of different drug analogue molecules or 'test' molecules (and these are illustrated in FIGS. 1, 4 and 6) to investigate the efficacy of binding said analogue molecules to the compound according to the first aspect or the carrier according to the second aspect, to thereby form the conjugate. To this end, the inventors determined Ki values of each drug conjugate synthesised, as described in Example 3.

The inventors also tested the transportation of the drug conjugate via the PepT1 pathway using efflux experiments, as described in Example 4. These drug analogue molecules did not have any biological activity, as they were merely test molecules. However, these drug analogue molecules or 'test' molecules were specifically chosen by the inventors to resemble biologically active drug molecules. Examples of different drug analogue 'test' molecules, which were attached to a compound according to the first aspect or the carrier according to the second aspect are shown as group Y in columns B and C of FIG. 1, and also in FIG. 6.

It will be appreciated that a number of the analogues tested by the inventors, as shown in FIGS. 1 and 6, are closely related to drugs in current use. For example, analogue B16 in FIG. 6 is a GABA analogue, and resembles a neurotransmitter; analogue B26 is a nicotinic acid analogue and resembles a nicotinamide, which may be used to lower cholersterol levels; analogue B28 is a stearic acid analogue, which is similar to anti-inflammatory prostaglandins; and analogue B30 is a cholic acid analogue, i.e. a steroid.

Therefore, it will be appreciated that it would be preferred to attach a biologically active drug molecule to the compound according to the first aspect or the carrier according to the second aspect. Hence, by way of example only, biologically active drug molecule which would be suitable for attachment to the thiopeptide according to the first aspect, the drug carrier according to the second aspect, or the drug conjugate according to the third aspect, include those possessing alcohol, thiol, acid or amino groups, for which subsequent hydrolysis would release the desired active drug. The advantages of conjugation include increased oral absorption of drugs with for example low solubility, or high polarity, control of their release (e.g. longer lasting analogues, or delayed release), and selective absorption by cells that express PepT1/PepT2 proteins (e.g. in the lung).

Examples of drugs that would be suitable for attachment to the thiopeptide carrier, and for which the conjugates that were synthesised and tested were chosen as models, include the following (for which "cf conjugate B/C", indicates the corresponding class of model compounds from FIG. 6):—

Antibiotics: norfloxacin, ciprofloxacin, ofloxacin (cf conjugates B)
Anticancer drugs: methotrexate (cf conjugates B)
taxol (cf conjugates C)
Antihistamines: cetirizine (cf conjugates B)
fexofenadine (cf conjugates B or C)
terfenadine (cf conjugates C)
Antihypertensives: valsartan, captopril (cf conjugates B)
losartan (cf conjugates C)
Anti-inflammatories: ibuprofen and related analogues (cf conjugates B)
prostaglandins and thromboxanes (cf conjugates C)
Antimalarials: quinine, and analogues such as mefloquine (cf conjugates C)
Antivirals: AZT, lamivudine, acyclovir (cf conjugates C)
Beta blockers: epinephrine, terbutaline, propranol (cf conjugates C)
Bronchodilators: adrenaline, salbutamol (cf conjugates C)
Cholersterol lowering agents: nicotinic acid (B26), acipimox (cf conjugates B)
compactin (cf conjugates C)
CNS drugs: adrenaline, apomorphine (cf conjugates C)
Sedatives: oxazepam, lorazepam, temazepam (cf conjugates C)
Steroids: analogues of estradiol, testosterone, cortisone (cf conjugates C)

Preferably, the drug comprises at least one functional group with which the functional group of the compound or drug carrier may react. As with above, the skilled technician will appreciate the types of functional or reactive groups, which would react with the compound or drug carrier. For example, the functional group on the drug molecule may comprise a carboxylic acid group or a hydroxyl group. Preferably, attachment of the drug to the compound of the first aspect or the drug carrier of the second aspect is by means of an ester linkage. Preferably, attachment of the drug occurs at residue 1 or 2 of the compound or drug carrier.

It is envisaged that attachment of the drug to the compound according to the first aspect or the drug carrier according to the second aspect may be by means of an ester linkage, or an ether linkage, or an amide linkage.

Changes to any of $R^1$, $R^2$, $R^3$, $R^4$, and/or $R^5$, in the Formulae given herein may make it possible to modify the compound or drug carrier in accordance with the invention so that any adverse features on the drug may be minimised by the nature of the first residue of the thiopeptide. Preferably, $R^1$ on the first amino acid residue (N-terminal) is suitable for such modification. For example, it may be beneficial to modify the net charge of the compound according to the first aspect, or the drug carrier according to the second aspect, such that the conjugate is pharmaceutically acceptable for use in medicine. For example, if the drug being attached to the compound or drug carrier is acidic, then it may be advantageous to neutralise the net charge of the compound-drug conjugate by using a basic compound or drug carrier. Hence, the net charge of the compound or drug carrier may be modulated by selection and/or modification of any of $R^1$, $R^2$, $R^3$, $R^4$, and/or $R^5$ groups. Preferably, the net charge may be modulated by selection and/or modification of the $R^1$ group.

It is also envisaged that it could be possible to selectively detach the drug molecule from the conjugate, by designing the compound or drug carrier so that the linkage between the compound/drug carrier and drug can be broken when the conjugate reaches its target environment or position ill vivo. For example, it is possible to design the thiopeptide drug carrier with appropriate amino acid residues such that the linkage with the drug can be broken when the conjugate is present in an acidic environment, for example, an area of wound tissue, which may have a low pH. Alternatively, some enzymes may only be expressed or be fully functional in certain tissues, and the thiopeptide-drug bond may be digested by such enzymes, when the conjugate reaches that particular tissue(s).

Accordingly, the compound according to the first aspect or the drug carrier according to the second aspect may be capable of being released or detached from the drug molecule.

Preferably, the compound is in the form of an L-isomer. Preferably, the or each amino acid is an L-isomer. Advantageously, use of an L-isomer improves the binding between the thiopeptide and the drug.

It will be appreciated that the drug conjugate is adapted to bind to PepT1 (or PepT2) carrier protein such that they have sufficient affinity for each other, wherein the binding therebetween is sufficiently strong such that the conjugate remains bound to the carrier protein during transportation using the PepT1 pathway, i.e. while being transported across the small intestine. In addition, the binding is sufficiently weak such that the conjugate can be detached from the carrier protein when it has been transported across the small intestine.

Accordingly, the drug conjugate may be adapted to bind with PepT1 protein or PepT2 protein with a Ki of between approximately 0.01-10 mM, and preferably, between approximately 0.05 mM-5 mM. It is preferred that the drug conjugate is adapted to bind with PepT1 protein or PepT2 protein with a Ki of between approximately 0.1-3 mM, more preferably, between approximately 0.2-1 mM, and most preferably between approximately 0.3 mM-7 mM. It is especially preferred that the Ki is about 0.5 mM±0.5 mM.

According to a fourth aspect of the invention, there is provided a conjugate according to the third aspect, for use as a medicament.

Preferably, there is provided use of the conjugate according to a third aspect for the preparation of an orally administrable medicament.

Preferably, the medicament or conjugate is orally administered to an individual. The medicament or conjugate may be adapted to be transported into the bloodstream via a PepT1/T2 pathway.

It will be appreciated that the medicament may be used to treat a wide variety of disease conditions, which will be determined by the nature of the drug attached to the thiopeptide. Examples of suitable drugs which may be carried by the thiopeptide are given above. Hence, by way of example only, the medicament may be used to treat cancer, allergic reactions, hypertension, inflammation, malaria, viral infection, bronchial infections, e.g. bronchitis.

It will be appreciated that the conjugate according to the third aspect of the present invention may be used in a monotherapy (i.e. use of the compound or derivatives thereof according to the invention alone). Alternatively, the conjugate according to the invention may be used as an adjunct, or in combination with, known therapies.

The conjugate according to the invention may be combined in compositions having a number of different forms depending, in particular on the manner in which the composition is to be used. Thus, for example, the composition may be in the form of a powder, tablet, capsule, liquid, gel, hydrogel, aerosol, spray, micelle, liposome or any other suitable form that may be administered to a person or animal. It will be appreciated that the vehicle of the composition of the invention should be one which is well tolerated by the subject to whom it is given, and preferably enables oral delivery of the compound.

Compositions comprising the conjugate according to the invention may be used in a number of ways. For instance, systemic administration is preferred, in which case the conjugate may be contained within a composition that is preferably ingested orally in the form of a tablet, capsule or liquid. Alternatively, it is possible that the composition may be administered by inhalation (e.g. intranasally). In some circumstances, the composition may be administered by injection into the blood stream. Injections may be intravenous (bolus or infusion) or subcutaneous (bolus or infusion).

The conjugate may also be incorporated within a slow or delayed release device. Such devices may, for example, be ingested and retained in the gut, and the conjugate may be released over weeks or even months. Such devices may be particularly advantageous when long-term treatment with the conjugate according to the invention is required and which would normally require frequent administration (e.g. at least daily injection).

Due to the 1:1 stoichiometry of the drug:conjugate, it will be appreciated that the amount of conjugate, and therefore drug, required in the conjugate according to the present invention, is determined by its biological activity and bioavailability, which in turn depends on the mode of administration, the physicochemical properties of the drug employed, and whether the drug is being used as a monotherapy or in a combined therapy. The frequency of administration will also be influenced by the above-mentioned factors and particularly the half-life of the conjugate within the subject being treated.

Optimal dosages to be administered may be determined by those skilled in the art, and will vary with the particular conjugate/drug in use, the strength of the preparation, the mode of administration, and the advancement of the disease condition. Additional factors depending on the particular subject being treated will result in a need to adjust dosages, including subject age, weight, gender, diet, and time of administration.

Known procedures, such as those conventionally employed by the pharmaceutical industry (e.g. in vivo experimentation, clinical trials, etc.), may be used to establish specific formulations of the compound according to the invention, and precise therapeutic regimes (such as daily doses and the frequency of administration).

Generally, a daily dose of between 0.01 µg/kg of body weight and 1.0 g/kg of body weight of the conjugate according to the invention may be used for the prevention and/or treatment of the specific medical condition. More preferably, the daily dose is between 0.01 mg/kg of body weight and 100 mg/kg of body weight. Daily doses may be given as a single administration (e.g. a single daily tablet). Alternatively, the conjugate may require administration twice or more times during a day. As an example, the conjugate according to the invention may be administered as two (or more depending upon the severity of the condition) daily doses of between 25 mgs and 5000 mgs. A patient receiving treatment may take a first dose upon waking and then a second dose in the evening (if on a two dose regime) or at 3 or 4 hourly intervals thereafter. Alternatively, a slow release device may be used to provide optimal doses to a patient without the need to administer repeated doses.

This invention provides a pharmaceutical composition comprising a therapeutically effective amount of a drug and the compound or drug carrier according to the present invention. In one embodiment, the amount of the conjugate is an amount from about 0.01 mg to about 800 mg. In another embodiment, the amount of the conjugate is an amount from about 0.01 mg to about 500 mg. In another embodiment, the amount of the conjugate is an amount from about 0.01 mg to about 250 mg. In another embodiment, the amount of the conjugate is an amount from about 0.1 mg to about 60 mg. In another embodiment, the amount of the conjugate is an amount from about 0.1 mg to about 20 mg.

This invention provides a process for making a pharmaceutical composition, the process comprising combining a therapeutically effective amount of a drug, the compound or drug carrier according to the present invention, and a pharmaceutically acceptable vehicle. A "therapeutically effective amount" is any amount of a drug which, when administered to a subject provides prevention and/or treatment of a specific medical condition. A "subject" is a vertebrate, mammal, domestic animal or human being.

A "pharmaceutically acceptable vehicle" as referred to herein is any physiological vehicle known to those of ordinary skill in the art useful in formulating pharmaceutical compositions. Preferably, the pharmaceutically acceptable vehicle, is adapted for oral administration. In a preferred embodiment, the pharmaceutical vehicle is a liquid and the pharmaceutical composition is in the form of a solution. In another embodiment, the pharmaceutically acceptable vehicle is a solid and the composition is in the form of a powder or tablet. In a further embodiment, the pharmaceutical vehicle is a gel and the composition is in the form of a cream or the like.

A solid vehicle can include one or more substances, which may also act as flavouring agents, lubricants, solubilisers, suspending agents, fillers, glidants, compression aids, binders or tablet-disintegrating agents; it can also be an encapsulating material. In powders, the vehicle is a finely divided solid that is in admixture with the finely divided active drug. In tablets, the drug is mixed with a vehicle having the necessary compression properties in suitable proportions and compacted in the shape and size desired. The powders and tablets preferably contain up to 99% of the active drug. Suitable solid vehicles include, for example, calcium phosphate, magnesium stearate, talc, sugars, lactose, dextrin, starch, gelatin, cellulose, polyvinylpyrrolidine, low melting waxes and ion exchange resins.

Liquid vehicles are used in preparing solutions, suspensions, emulsions, syrups, elixirs and pressurized compositions. The active drug can be dissolved or suspended in a pharmaceutically acceptable liquid vehicle such as water, an organic solvent, a mixture of both or pharmaceutically acceptable oils or fats. The liquid vehicle can contain other suitable pharmaceutical additives such as solubilisers, emulsifiers, buffers, preservatives, sweeteners, flavouring agents, suspending agents, thickening agents, colours, viscosity regulators, stabilizers or osmo-regulators. Suitable examples of liquid vehicles for oral and parenteral administration include water partially containing additives as above, e.g. cellulose derivatives, preferably sodium carboxymethyl cellulose solution), alcohols (including monohydric alcohols and polyhydric alcohols, e.g. glycols) and their derivatives, and oils (e.g. fractionated coconut oil and arachis oil). For parenteral administration, the vehicle can also be an oily ester such as ethyl oleate and isopropyl myristate. Sterile liquid vehicles are useful in sterile liquid form compositions for parenteral administration. The liquid vehicle for pressurized compositions can be halogenated hydrocarbon or other pharmaceutically acceptable propellent.

In some cases, where it is desired to inject the conjugate, liquid pharmaceutical compositions which are sterile solutions or suspensions can be utilized by for example, intramuscular, intrathecal, epidural, intraperitoneal, intravenous and particularly subcutaneous, intracerebral or intracerebroventricular injection. The drug may be prepared as a sterile solid composition that may be dissolved or suspended at the time of administration using sterile water, saline, or other appropriate sterile injectable medium. Vehicles are intended to include necessary and inert binders, suspending agents, lubricants, flavourants, sweeteners, preservatives, dyes, and coatings.

The conjugant according to the invention can be administered orally in the form of a sterile solution or suspension containing other solutes or suspending agents (for example, enough saline or glucose to make the solution isotonic), bile salts, acacia, gelatin, sorbitan monoleate, polysorbate 80 (oleate esters of sorbitol and its anhydrides copolymerized with ethylene oxide) and the like. Preferably, the conjugate according to the invention is administered orally either in liquid or solid composition form. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

According to a fifth aspect, there is provided an assay adapted to detect transportation of a conjugate according to the third aspect from a first side of a membrane to a second side of a membrane, the assay comprising detection means adapted to detect the presence of the conjugate on first and second sides of the membrane.

The membrane may be present in the stomach, liver, brain, or the kidneys. Preferably, the membrane is present in the intestine, more preferably, the small intestine and most preferably, the jejunum of the small intestine.

The detection means may be adapted to detect UV absorption of the thiopeptide, preferably, high UV absorption thereof. The UV absorption may be detected by, for example, using HPLC. In this way, the detection means may be used to detect a thiopeptide conjugate in cells or vesicles.

The compound according to the first aspect of the invention or the drug carrier according to the second aspect of the invention may be synthesised using common known chemical synthesis techniques. An example method for synthesising the compound or drug carrier according to the invention is disclosed in FIGS. 3 and 4, and is discussed in the Example.

It will be appreciated by the skilled technician that there are many ways that the compound and drug carrier according to the invention could be made. However, the sulphur atom of the thio-functional group causes potential problems with the molecule, and the method disclosed herein provides an effective solution. It will be appreciated that small changes to any of the steps of the synthesis disclosed herein may be made while still benefiting from the invention.

According to a sixth aspect, there is provided a method of treating an individual, the method comprising administering to an individual in need of such treatment, a drug conjugate according to the third aspect.

Preferably, the drug conjugate comprises a drug molecule attached to a compound according to the first aspect or a drug carrier according to the second aspect.

All of the features described herein (including any accompanying claims, abstract and drawings), and/or all of the steps of any method or process so disclosed, may be combined with any of the above aspects in any combination, except combinations where at least some of such features and/or steps are mutually exclusive.

For a better understanding of the invention, and to show how embodiments of the same may be carried into effect, reference will now be made, by way of example, to the accompanying drawings, in which:—

BRIEF DESCRIPTION OF THE FIGURES

FIG. 7 shows a table summarising the various thiopeptide conjugates shown in FIG. 6, and respective binding data (Ki values), and efflux transport data, for each conjugate where available;

EXAMPLE 1

Making Thiopeptides Compounds According to the Invention

The aim of the present invention was to make a drug carrier compound, which enables the preparation of drug-drug carrier conjugates, which would allow the oral administration of drugs that are not currently administrable by mouth. In addition, such drug-drug carrier conjugates could also be used to improve the efficacy of drugs which are currently administered orally, but which show decreased levels of biological activity when administered by mouth. In order to achieve this aim, the following steps were carried out:— a) A range of thiopeptide drug carrier analogues were prepared;

b) Methods for synthesising the drug carriers were developed, both to facilitate the rapid synthesis of a wide range of analogues, and also to enable the preparation of the drug carrier cheaply and on a large scale;

c) Bio-assays were developed to test the efficacy of the drug carrier analogues;

d) A transport bioassay was developed that works quickly, and with small amounts of the drug substrate;

e) The in vivo transportation of a non-orally available medicine by PepT1 across the lining of the gut was demonstrated.

1) Preparation of a Range of Thiopeptide Carrier Molecules

Figure 2:
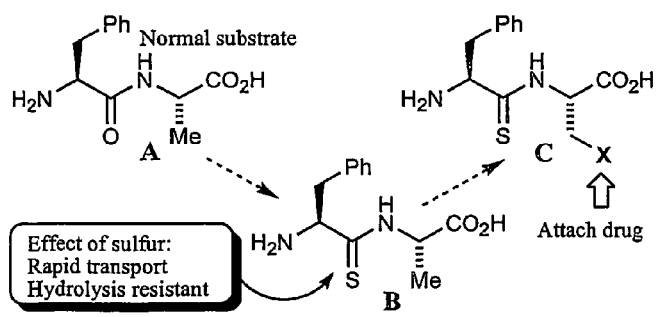
FIG. 2 summarises how a compound according to the first aspect of the invention or a drug carrier according to the second aspect of the invention relate to natural dipeptide substrates for PepT1.

The inventors based their work on a 3D substrate model of a substrate, shown as structure A, for the PepT1 protein, which is shown in FIG. 2. While attempting to refine the proposed PepT1 substrate model shown in FIG. 2, a thiopeptide analogue drug carrier as shown as structure B in FIG. 2 was prepared. The inventors were surprised to discover that Structure B exhibits three main advantageous features namely (i) it binds efficiently to PepT1 (Ki 0.3 mM, typical natural substrates, in vitro assay); (ii) it is rapidly transported in vivo; and (iii) it is resistant to hydrolysis, unlike most peptides. Hence, the thiopeptide shown as structure B in FIG. 2 was believed to be a potential carrier for drugs that do not naturally diffuse across the villi of the small intestine, or that have poor solubility, provided that a method of attaching a drug to compound B at position X, could be devised. Accordingly, serine, aspartate or glutamate analogues of compound C as shown in FIG. 2 were made, in which X is hydroxy or carboxylic acid group, connected to the drug via an ester linkage, thereby forming a drug conjugate.

2) Preparation of a Protected Thiopeptide Serine Drug Carrier

Figure 3:
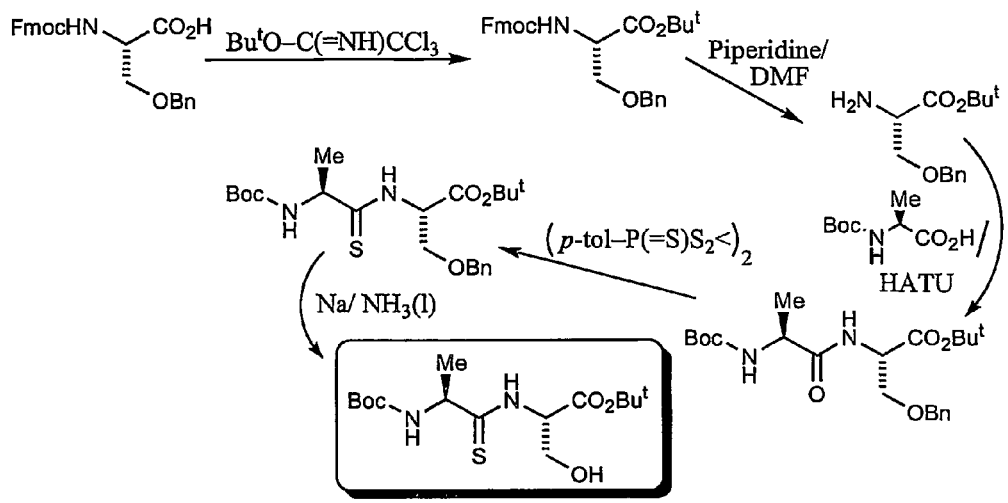
FIG. 3 shows a schematic diagram for the synthesis of a protected thiopeptide serine drug carrier in accordance with the invention.

A method was then devised for preparing a set of thiopeptide carriers that are suitably protected for the attachment of drugs that possess a carboxylic acid reactive group. The method of synthesising a protected thiopeptide serine drug carrier compound is summarized in FIG. 3. The particular strategy and choice of protecting groups were designed to enable the preparation of large amounts of drug carrier molecules, to which a drug molecule could then be attached. Suitable protection groups include t-butyl, benzyl, methoxybenzyl, allyl or fluorenyl attached to nitrogen, oxygen or sulphur via ester, thioether, or carbamate linkages.

The final step before attachment of a drug to the carrier molecule, is the deprotection of the functional group on the carrier to which the drug molecule is to be attached. This is achieved by the addition of $Na/NH_3$ (liquid), i.e. sodium/liquid ammonia (or similar one electron reducing agents), for the removal of benzyl-type protection, thereby freeing up the functional group ready for attachment of the drug.

Following attachment of the drug to the drug carrier/compound in accordance with the present invention, the conjugate was then globally deprotected. This method has enabled the preparation of a large range of drug-carrier conjugates very quickly.

3) Preparation of a Drug Conjugate

Figure 4:
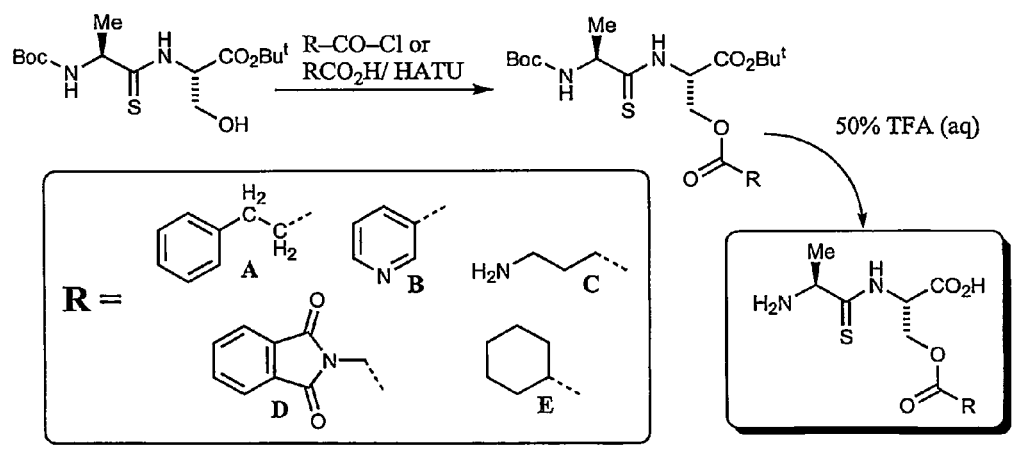
FIG. 4 shows a schematic diagram for the synthesis of a drug conjugate in accordance with the third aspect of the present invention.

Referring to FIG. 4, there is shown the successful attachment of a range of carboxylic acids, which acted as 'test' drug molecules to the drug carrier thiopeptide produced in (2) above. Following attachment of the carboxylic acid 'test' molecule to the drug carrier, the conjugate was then deprotected so that the efficacy of transportation could be investigated. Conjugates A, B, D and E shown in FIG. 4 have been demonstrated to all bind well to PepT1 (see Example 3 below). In addition, actual transportation of analogue E by the PepT1 pathway has also been shown (see Example 4 below).

Figure 6:
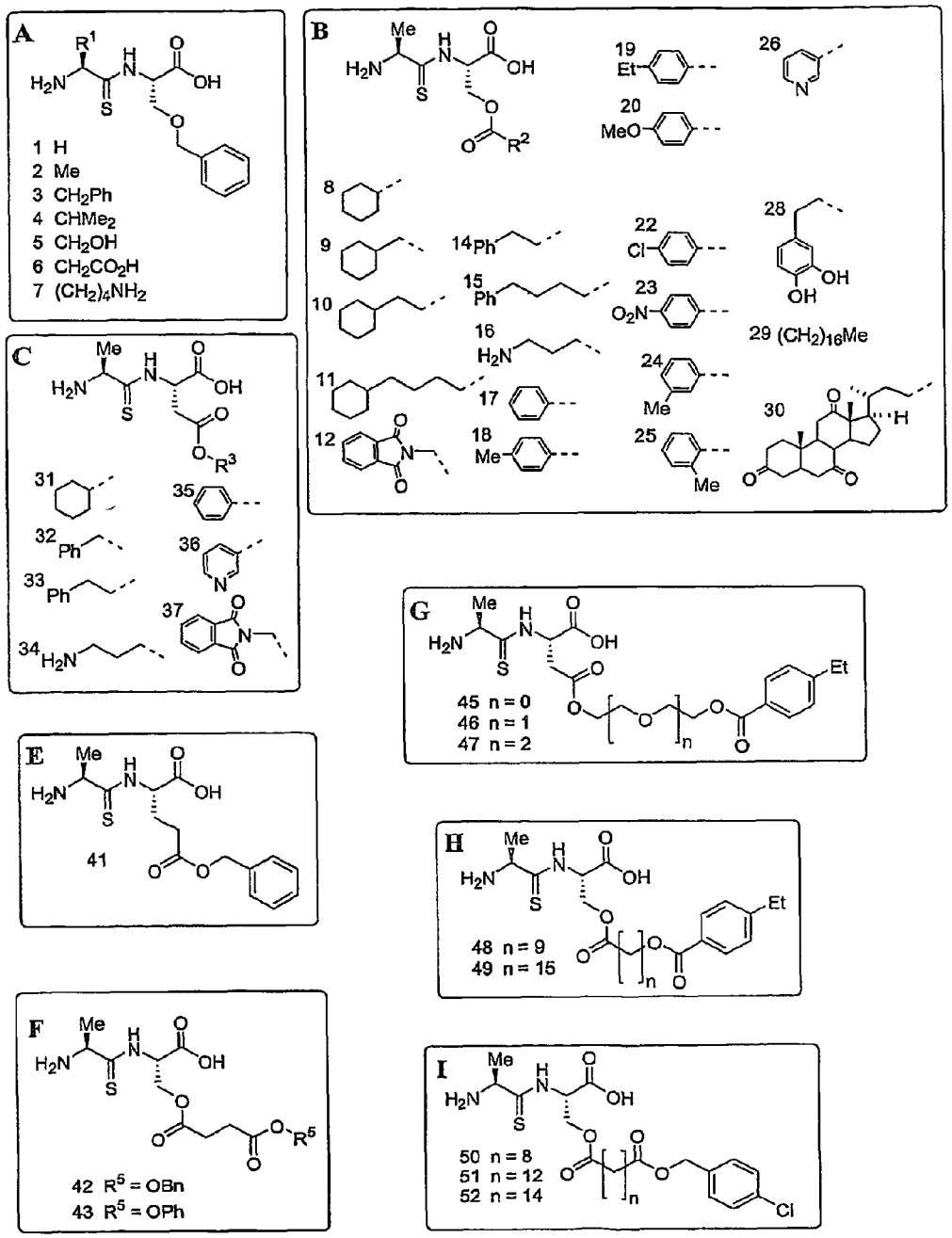
FIG. 6 shows further variations in thiopeptide conjugates that may be tested in accordance with the third aspect of the invention.

The inventors went on to synthesise a large number of thiopeptide-drug analogue conjugates, which were tested for binding to PepT1, and also transportation by the PepT1 pathway (efflux transport). Referring to FIG. 6, there are shown chemical structures of 45 thiopeptide-drug analogue conjugates. The conjugates are divided in to 8 groups, A-I:—

Group A (1A-7A) represents a thiodipeptide comprising a phenylmethyl group attached to an oxygen atom on the second amino acid residue of a thiodipeptide carrier, in which the $R^1$ group on the first amino acid residue is varied as shown by numbers 1-7;

Group B (8B-30B) represents a thiodipeptide comprising alanine as the first amino acid residue, and serine as the second amino acid residue, to which various $R^2$ groups (i.e. the drug analogues) are bound;

Group C (31C-34C) represents a thiodipeptide comprising alanine as the first amino acid residue, and aspartate as the second amino acid residue, to which various $R^3$ groups (i.e. the drug analogues) are bound;

Group E (41E) represents a thiodipeptide comprising alanine as the first amino acid residue, and glutamate as the second amino acid residue, bound to the drug analogue as shown.

Group F (23F & 43F) represents a thiodipeptide comprising alanine as the first amino acid residue, and serine as the second amino acid residue, to which various $R^5$ groups (i.e. the drug analogues) are bound;

Group G (45G-47G) represents a thiodipeptide comprising alanine as the first amino acid residue, and aspartate as the second amino acid residue, in which the length of the spacer chain [—$CH_2$—O—$CH_2$—] is varied from n=0, 1, or 2 as shown, and are linked to a drug analogue;

Group H (48H & 49H) represents a thiodipeptide comprising alanine as the first amino acid residue, and serine as the second amino acid residue, in which the length of the spacer chain [—$CH_2$—] is varied from n=9 or 15, and are linked to a drug analogue; and Group I (50I-52I) represents a thiodipeptide comprising alanine as the first amino acid residue, and serine as the second amino acid residue, in which the length of the spacer chain [—$CH_2$—] is varied from n=8, 12, or 14, and are linked to a drug analogue.

Referring to FIG. 7, there is shown a table summarising the data for each conjugate. Hence, the table shows Ki binding data for each conjugate synthesised, and also efflux transport data for a large proportion of the conjugates synthesised. In addition, the inventors also investigated the efficacy of analogues or derivatives of a compound in accordance with the first aspect of the invention, i.e. a hydrolysis resistant thiopeptide. They prepared a thiopeptide drug conjugate in which the first amino acid residue was a D-isomer, i.e. D-Ala-ΨS-Ser(OBn), and not an L-isomer.

With reference to the codes for each conjugate used in FIG. 6, conjugate A shown in FIG. 4 corresponds to B14 (shown in FIG. 6), conjugate B shown in FIG. 4 corresponds to B26 shown in FIG. 6, conjugate C corresponds to B16, conjugate D corresponds to B12, and conjugate E corresponds to B8.

EXAMPLE 2

The Relevance of the Thio-Group Compounds According to the Invention

In vivo transport experiments, using the methodology described in Lister et al. (*J. Physiol.*, 1995, 484.1, 173-182), were used to investigate the importance of the thio group in the compounds according to the invention during transport of thiopeptides across the gut wall. Hence, the inventors prepared a test thiopeptide, Phe-ΨS-Ala, i.e. the thiodipeptide of phenylalanine and alanine. For the purposes of this experiment, this thiopeptide was not conjugated to a drug analogue molecule. Then, using rat jejenum, they carried out direct measurements of transport of this test thiopeptide across the gut wall. A normal dipeptide, D-Phe-L-Ala (a standard, non-hydrolyzable dipeptide) was used as control. The results indicated that the thiopeptide is transported more efficiently than the non-thio control compound dipeptide, as detected by HPLC analysis:— a) 1 mM of D-Phe-L-Gln (non-thio dipeptide control) is transported at 0.244 (+/−0.036) micromol/min/g of whole dry intestine.

b) 1 mM of the thiopeptide analogue of L-Phe-L-Ala is transported at 3.09 (+/−0.047) micromol/min/g of whole dry intestine.

The results clearly demonstrate not only that the thiopeptide is recognized by PepT1, and is a substrate thereof, but also:—

(a) that the PepT1 transport mechanism still operates; and
(b) that the thiopeptide is resistant to the peptidases that are present in and around the villi of the small intestine, due to the lack of a peptide bond (i.e. it has been substituted with a thio bond).

The data show that the thiopeptide is therefore transported at about 13 times the rate of the control dipeptide D-Phe-L-Gln, which does have a peptide bond, which is degraded by peptidases.

EXAMPLE 3

Binding of Thiopeptide-drug Conjugates to PepT1 Protein

Uptake of the radiolabelled dipeptide [$^3$H]-D-Phe-L-Gln (17.4 Ci/mmole, custom synthesised, Cambridge Research Biochemicals, Stockton-on-Tees, UK) in competition with the compounds to be tested, was performed as previously described (Meredith et al. *J. Physiol.*, 1998, 512, 629-634). Briefly, 5 oocytes were incubated at room temperature in 100 μL of uptake medium (95 mM NaCl, 2 mM KCl, 1 mM CaCl$_2$, 0.42 mM MgCl$_2$, 10 mM Tris/Mes pH 5.5) with tracer (0.4 μM) [$^3$H]-D-Phe-L-Gln with or without a test compound at the appropriate concentration. After incubation for one hour, the oocytes were washed sequentially five times in 1 mL of ice-cold uptake medium, then lysed individually with 100 μL 2% (w/v) SDS in vials, and liquid scintillation counted.

Quantitative binding data has been produced for a large number of thiodipeptide carriers with attached drug surrogates using the methodology described in Meredith et al., 1998, discussed supra, and is shown in Table 2 below, and in FIG. 7. The five compounds shown in Table 2 are E (209), B (210), A (211), D (212) and C (213), as shown in FIG. 4. Each of the thiopeptide carrier molecules shown is in accordance with the present invention, with each compound comprising a serine amino acid side chain group on the second amino acid residue.

TABLE 2

Binding data for thiopeptide carrier/drug conjugates

| Compound number | $K_i$ |
|---|---|
| 209 (B8) | 0.30 +/− 0.06 mM |
| 210 (B26) | 0.36 +/− 0.11 mM |
| 211 (B14) | 0.10 +/− 0.04 mM |
| 212 (B12) | 0.027 +/− 0.006 mM |
| 213 (B16) | 0.60 +/− 0.13 mM |

The code in brackets following each number in Table 2 above, is the corresponding conjugate code for each compound used in FIG. 6.

Figure 5:
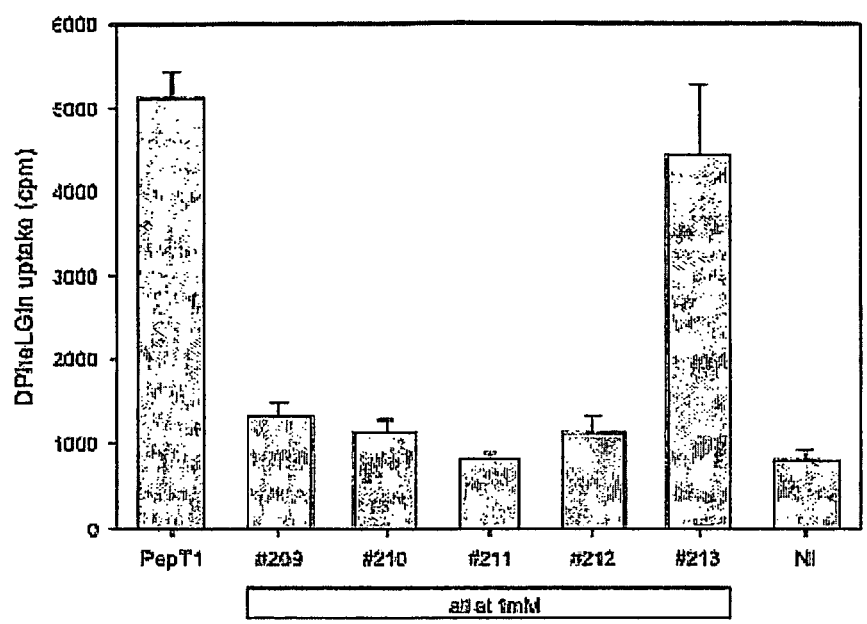
FIG. 5 shows a bar graph showing binding data for a drug carrier according to the second aspect of the invention.

The data are also presented in the bar chart illustrated as FIG. 5. The Ki binding values for these test carrier drug conjugates range from between 0.02 mM to 0.6 mM. Accordingly, the binding data for each conjugate according to the invention illustrates that they are good substrates for PepT1 carrier protein.

Figure 8A:
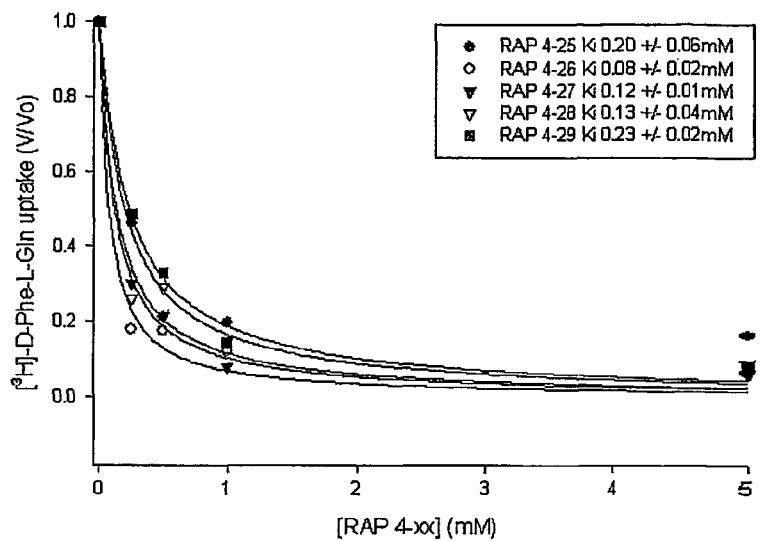
FIGS. 8a and 8b show exemplary data for the determination of the $K_i$ values of thiopeptide analogues in accordance with the invention, in which compound RAP4-25 corresponds to B18; RAP4-26 to B24; RAP4-27 to B25; RAP4-28 to B19; RAP4-29 to B17; RAP4-30 to B23; RAP4-31 to B22; RAP4-32 to F42; RAP4-33 to F43; and RAP4-34 to B20.
Figure 8B:
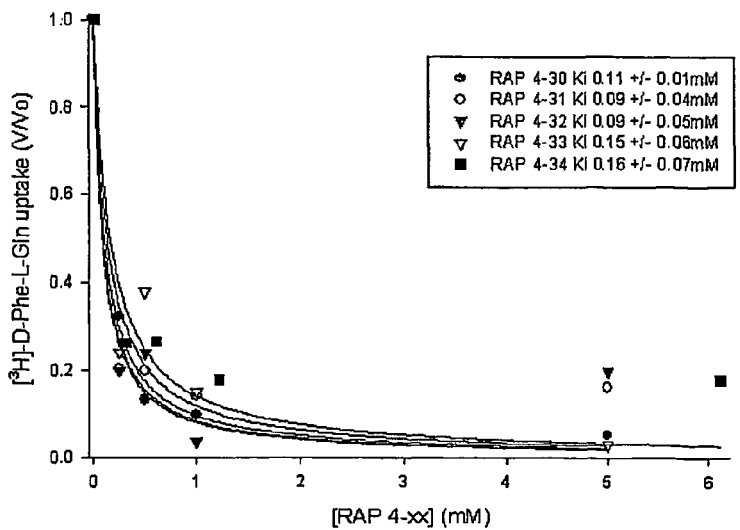

Referring to FIGS. 8*a* and 8*b*, there are shown some additional exemplary data illustrating the determination of the Ki values of a number of thiopeptides conjugated to different drug analogues. The compound codes given in FIGS. 8*a* and 8*b* correspond to the following analogues: RAP4-25: B18; RAP4-26: B24; RAP4-27: B25; RAP4-28: B19; RAP4-29: B17; RAP4-30: B23; RAP4-31: B22; RAP4-32: F42; RAP4-33: F43; and RAP4-34: B20.

With reference to the table in FIG. 7, there is shown the corresponding Ki value for each conjugate prepared in this study.

EXAMPLE 4

Transport of Thiopeptides Using an Efflux Assay

Efflux experiments were performed as described in Temple et al., *J. Biol. Chem.*, 1998, 273, 20-22. Briefly, PepT1-expressing oocytes were micro-injected with 4.6 nl of [$^3$H]-D-Phe-L-Gln (17.4 Ci/mmole) and allowed to recover for 15 minutes. 5 oocytes were incubated in 10 μL uptake solution (pH 5.5) containing a potential substrate (i.e. a thiodipeptide-drug analogue conjugate) at 10 mM, with a negative control (i.e. uptake solution pH 5.5) and a positive control (i.e. 20 mM dipeptide Gly-Gln in pH 5.5 uptake solution). After 90 minutes incubation at room temperature, 50 μL of the medium was removed and placed in a scintillation vial for counting. The oocytes were washed sequentially five times in 1 mL of ice-cold uptake medium, then lysed individually with 100 μL 2% (w/v) SDS in vials, and liquid scintillation counted.

Efflux of the radiolabelled dipeptide is a positive indication of active transport via PepT1. However, it should be appreciated that negative efflux results do not necessarily means that substrates are not transported via PepT1, as it is dependent on the Ki value of a specific conjugate to PepT1 protein.

In the assays carried out, the dipeptide Gly-Gln (which is known to be transported by PepT1) caused about 30% of labelled D-Phe-L-Gln to remain in the oocytes. At the same concentration, the test substrates (the conjugates being tested) are assessed as follows:—

<(measureable efflux, but less transport than Gly-Gln control, with ≥50% of D-Phe-L-Gln remaining)

=(efflux similar to the effect of Gly-Gln, i.e. 25-50% of labelled D-Phe-L-Gln remaining)

>(more efflux than Gly-Gln, i.e. <25% of labelled D-Phe-L-Gln remaining)

A summary of the efflux transport data carried out is shown in FIG. 7. It can be seen that the following conjugates were transported better than Gly-Gln, which is known to be transported in vivo:—B22, G45, G46, and I50. The following conjugates were transported as well as the control peptide Gly-Gln: B8, B9, B10, B11, B15, B20, B25, B30, F43, G47, H48, H49, and I52. Finally, the following conjugates were transported (although less rapidly than the control peptide under experimental conditions): B12, B14, B16, B17, B19, B23, B26, B29, C36, F42, and I51. However, it will be appreciated that even though transporation for this conjugates is less than the control, transportation using the PepT1 pathway has still been demonstrated, and that the thiopeptides are still exhibit transport efficacy.

Compound 209 (E shown in FIG. 4; B8 shown in FIG. 6) was tested for transport using a trans-stimulation assay using the methodology described in Temple (*J. Biol. Chem.*, 1998, 273, 20-22), from which the efflux of radio-labelled control dipeptide, D-Phe-L-Gln, indicated that it was indeed transported. There are no reports in the literature of thiodipeptides attached to drugs or drug analogues, and therefore no examples of such conjugates being actively transported.

Accordingly, the inventors of the present invention have shown that Compound 209 (E):— a) Inhibits uptake of D-Phe-L-Gln by 88% (+/−1.4) at 1 mM, and gave a Ki of 0.3 mM (+/−0.06); and b) At 2 mM, Compound 209 (E) gave 54% efflux compared to 72% for 10 mM Gly-Gln, indicating that it is transported more efficiently than Gly-Gln.

The transport data were measured as average cpm (counts per minute) from 5 experiments:—

Control 4852 (+/−89) cpm remaining in oocytes
10 mM Gly-Gln 1347 (+/−126)
2 mM conjugate 2237 (+/−594)

Figure 1:
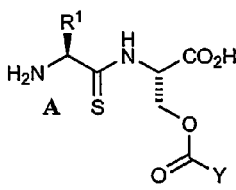
FIG. 1 represents a Table showing variations in thiopeptide conjugates that might be tested in accordance with the third aspect of the invention.

In addition to these aforementioned thiopeptide analogues, additional analogues were prepared as shown in FIGS. 1 and 6. It should be noted that two of the modifications (structure B in column A, and all of column D of FIG. 1) relate to the drug carrier compound itself, and therefore necessitate changes early in the synthesis. These latter two modifications are important from a drug delivery standpoint, because changes to the side-chain of the first amino acid residue in the thiopeptide allows the 'fine-tuning' of the drug delivery system so that any adverse features on the drug are off-set by the nature of amino acid residue 1; for example, if there were preferred overall neutrality of the drug-drug carrier conjugate at pH 5.5. Changing the second amino acid residue to aspartate enables the attachment of drugs possessing a hydroxyl function, which leads to a massive increase in the potential number of drugs that might be suitable for attachment to the carrier.

Figure 9A:
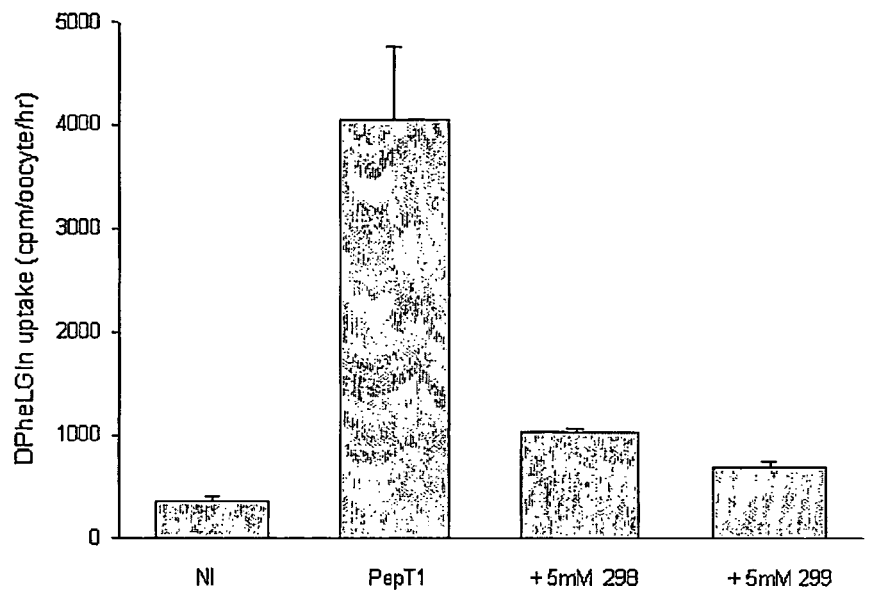
FIGS. 9a and 9b show exemplary data for binding/efflux of thiopeptide analogues in which compound code 298 corresponds to B30, and code 299 corresponds to B29.
Figure 9B:
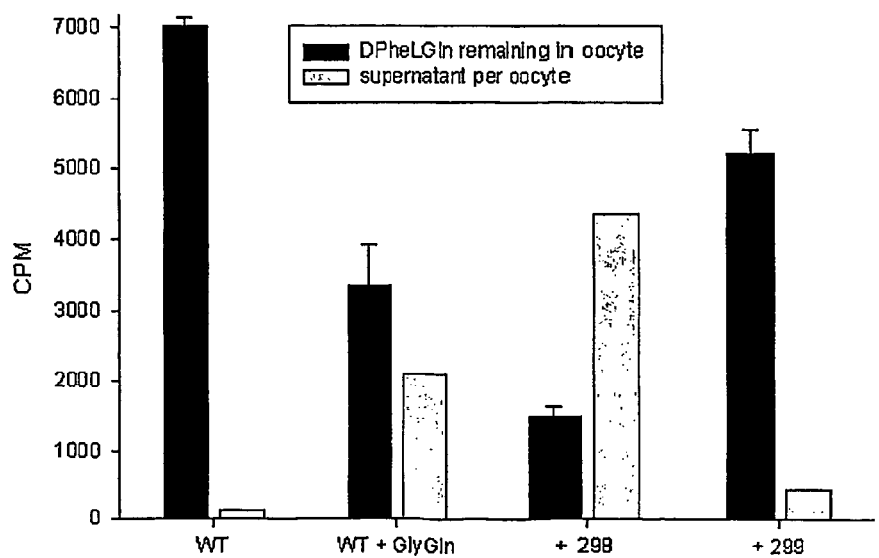

Referring to FIGS. 9a and 9b, there are shown exemplary data of the inhibition of D-Phe-L-Gln for compounds B29 (299) and B30 (298). These were single concentration binding/efflux experiments, for which the 5 mM solution of substrate was filtered (due to low solubility), before being tested for inhibition (as shown in FIG. 9a) or efflux (as shown in FIG. 9b). Compound B30 is a steroid, and the inventors were very surprised (and pleased) to see that the thiopeptide carrier could conjugate with such a molecule, and that efflux transportation studies showed that it is transported by the PepT1 pathway, i.e. efflux similar to the control dipeptide Gly-Gln.

As mentioned above, the inventors also investigated the efficacy of analogues or derivatives of a compound in accordance with the first aspect of the invention, and prepared thiopeptide drug conjugates in which the first amino acid residue was a D-isomer: D-Ala-ΨS-Ser(OBn). This D-isomer analogue was a substrate for PepT1 and had a Ki of 1.07 mM. In addition, the D-isomer analogue was more hydrolysis resistant than its corresponding L-isomer.

EXAMPLE 5

Single Dose Toxicity Study in Rat

Toxicity testing required about 5 g of the thiodipeptide, Ala-ΨS-Ser.tfa (trifluoroacetate salt), which was delivered to rats as test subjects.
Study Design:
Single oral dose of 700 mg/kg to 5 males and 5 females on day 1.

| Clinical observations: | daily for 15 days |
| --- | --- |
| Bodyweights: | days 1, 8 and 15 |
| Scheduled termination: | day 15 |

Test Substance Formulation:
The dose formulation was successfully prepared using physiological saline as the vehicle. The concentration of the test substance was 140 mg/ml, dosed at a volume of 5 ml/kg, resulting in a dose of 700 mg/kg.
Intercurrent Deaths:
There were no intercurrent deaths.
Clinical Observations:
There were no treatment related findings.
Bodyweights:
All animals had gained weight on 15.
Macroscopic Findings at Scheduled Termination:
There were no macroscopic findings at scheduled termination, which were considered to be related to treatment.

CONCLUSION

In conclusion, the experiments and data described herein illustrate the efficacy of the thiopeptide compound in accordance with the invention as a drug carrier molecule, and how drug-carrier conjugates may be transported across membranes in vivo using the PepT1 protein. The drug analogues used, as shown in FIG. 6, had strong similarities with the structure of biologically active drug molecules, for example, the steroid analogue (B30). Hence, the inventors designed and synthesised a large number of thiopeptide-drug analogue conjugates. The Ki values with binding to PepT1 protein were then determined. The results indicate that they would act as good substrates to PepT1/PepT2. In addition, the inventors have tested the transportation of a large number of the conjugates using efflux studies. These studies show that the conjugates are successfully transported by the PepT1 pathway. Finally, the toxicity data shown herein illustrate that the thiopeptide-analogue conjugates are not toxic to rats under test.

The invention claimed is:

1. A drug conjugate comprising a drug molecule covalently bonded to a thiodipeptide, the thiodipeptide having the formula

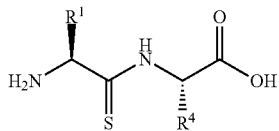

wherein the drug molecule is covalently bonded to a functional group of $R^4$, and is selected from the group consisting of an antibiotic, an anticancer drug, an antihistamine, an antihypertensive, an anti-inflammatory, an antimalarial, an antiviral, a beta blocker, a bronchodilator, a cholesterol lowering agent, a Central Nervous System (CNS) drug, a sedative, and a steroid, wherein $R^4$ is a side chain group of serine, glutamic acid, or aspartic acid, wherein $R^1$ is independently selected from a group consisting of:
a hydrogen; and
a methyl.

2. The drug conjugate of claim 1, wherein $R^4$ comprises a spacer which is constructed and arranged to distance the drug from the thiopeptide when bound thereto.

3. The drug conjugate of claim 2, wherein the spacer comprises an alkyl chain, or an alkyl chain incorporating ether, amino, ester, amide or carbonyl groups, with a terminal group for attachment to the thiopeptide compound and the drug.

4. The drug conjugate of claim 2, wherein the spacer comprises [—$CH_2$—]$_n$, wherein the value of n is an integer of at least 1.

5. The drug conjugate of claim 2, wherein the spacer comprises [—$CH_2$—O—$CH_2$—]$_n$, wherein n is an integer of at least one.

6. A drug conjugate according to claim 1, wherein covalent attachment of the drug molecule to the thiopeptide is by means of an ester linkage, ether linkage or an amide linkage.

7. The drug conjugate of claim 1 wherein the drug is selected from the group consisting of oxazepam, lorazepam and temazepam.

8. The drug conjugate of claim 1 wherein the N-terminal residue of the thiodipeptide is an L-isomer.

9. The drug conjugate of claim 1 wherein the C-terminal residue of the thiodipeptide is an L-isomer.

10. The drug conjugate of claim 1 wherein the N- and C-terminal residues of the thiodipeptide are L-isomers.

11. A drug conjugate molecule, being a product of the reaction of a functional group of a thiodipeptide with a drug molecule, wherein the thiodipeptide has the formula:

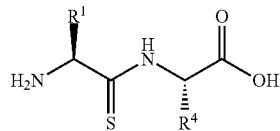

in which $R^4$ comprises the functional group that reacts with the drug molecule to covalently attach the drug molecule to the thiodipeptide,
wherein $R^4$ is
a side chain group of serine, glutamic acid, or aspartic acid, wherein $R^1$ is independently selected from a group consisting of:
a hydrogen; and
a methyl;
wherein the drug molecule is selected from the group consisting of an antibiotic, an anticancer drug, an antihistamine, an antihypertensive, an anti-inflammatory, an antimalarial, an antiviral, a beta blocker, a bronchodilator, a cholesterol lowering agent, a Central Nervous System (CNS) drug, a sedative, and a steroid.

* * * * *